US008652438B2

(12) United States Patent
Nomoto et al.

(10) Patent No.: US 8,652,438 B2
(45) Date of Patent: Feb. 18, 2014

(54) CENTRAL NERVOUS SYSTEM LABELLING COMPOSITION FOR INTRANASAL ADMINISTRATION AND LABELLING METHOD AND SCREENING METHOD USING CENTRAL NERVOUS SYSTEM LABELLING COMPOSITION FOR INTRANASAL ADMINISTRATION

(75) Inventors: Tsuyoshi Nomoto, Tokyo (JP); Kohei Watanabe, Yokohama (JP); Taichi Shintou, Saitama (JP); Takeshi Miyazaki, Yokohama (JP); Toshio Tanaka, Tsu (JP); Yuhei Nishimura, Tsu (JP); Yasuhito Shimada, Tsu (JP)

(73) Assignee: Canon Kabushiki Kaisha, Tokyo (JP)

( * ) Notice: Subject to any disclaimer, the term of this patent is extended or adjusted under 35 U.S.C. 154(b) by 35 days.

(21) Appl. No.: 13/084,971

(22) Filed: Apr. 12, 2011

(65) Prior Publication Data

US 2011/0182810 A1 Jul. 28, 2011

Related U.S. Application Data

(63) Continuation of application No. PCT/JP2010/007465, filed on Dec. 24, 2010.

(30) Foreign Application Priority Data

Dec. 25, 2009 (JP) .................................. 2009-296329

(51) Int. Cl.
*A61K 51/00* (2006.01)
*A61M 36/14* (2006.01)

(52) U.S. Cl.
USPC .......................................... 424/1.65; 424/9.6

(58) Field of Classification Search
None
See application file for complete search history.

(56) References Cited

U.S. PATENT DOCUMENTS

| 2003/0138791 A1* | 7/2003 | Haalck et al. ................. 435/6 |
| 2005/0281741 A1* | 12/2005 | Achilefu et al. ............ 424/1.69 |
| 2006/0193776 A1 | 8/2006 | Goldsmith et al. |
| 2009/0087385 A1* | 4/2009 | Di Mauro ...................... 424/43 |
| 2010/0166663 A1 | 7/2010 | Nomoto et al. |

FOREIGN PATENT DOCUMENTS

| JP | 4-147131 A | 5/1992 |
| JP | 2000-344684 A | 12/2000 |
| JP | 2000344684 A * | 12/2000 |
| JP | 2010-168369 A | 8/2010 |
| JP | 2010-169677 A | 8/2010 |
| WO | 2007/063950 A1 | 6/2007 |
| WO | 2010/074325 A1 | 7/2010 |

OTHER PUBLICATIONS

Mathison et al. J. Drug Targ. 1998, 5, 415-441.*
Chang et al. J. Med. Chem. 2009, 52, 3539-3547.*
Bettina C. Lieberoth et al., "Double Labeling of Neurons by Retrograde Axonal Tracing and Non-radioactive in Situ Hybridization in the CNS of Adult Zebrafish," Methods in Cell Science 25: 65-70 (2003).
Axel Nimmerjahn et al., "Sulforhodamine 101 as a Specific Marker of Astroglia in the Neocortex in Vivo," Nature Methods, vol. 1, No. 1, pp. 31-37 (Oct. 2004).
Raimon Sabate et al., "Pinacyanol as Effective Probe of Fibrillar β-Amyloid Peptide: Comparative Study with Congo Red," Biopolymers, vol. 72, No. 6, pp. 455-463 (2003).
International Preliminary Report on Patentability in International Application No. PCT/JP2010/007465 (Jun. 2012).
Jiong Shi et al., "Labeling of Cerebral Amyloid β Deposits In Vivo Using Intranasal Basic Fibroblast Growth Factor and Serum Amyloid P Component in Mice," 43(8) J. Nucl. Med. 1044-1051 (Aug. 2002).
Extended European Search Report in European Application No. 10838971.9 (dated Oct. 18, 2013).

* cited by examiner

*Primary Examiner* — Michael G Hartley
*Assistant Examiner* — Sean R Donohue
(74) *Attorney, Agent, or Firm* — Fitzpatrick, Cella, Harper & Scinto

(57) ABSTRACT

There is provided a central nervous system labelling composition for intranasal administration for the purpose of labelling the central nervous system from the olfactory epithelium by way of the olfactory bulb and by means of intranasal administration. Additionally, there is provided a method of non-invasively labelling the central nervous system by way of an administration route that entails little transferability to the entire body. Furthermore, there is provided a screening method using a central nervous system labelling composition for intranasal administration. A central nervous system labelling composition for intranasal administration is characterized by labelling the central nervous system from the olfactory epithelium by way of the olfactory bulb and by means of intranasal administration and by containing at least one compound expressed either by the general formula (1) or the general formula (2) shown below as effective component:

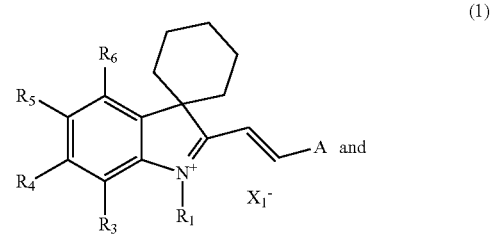

(1)

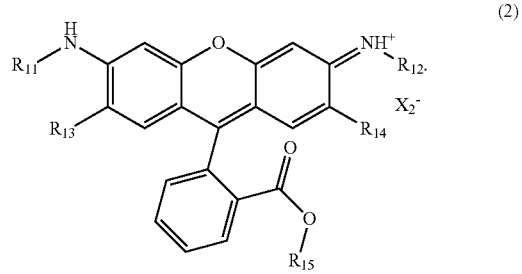

(2)

6 Claims, 11 Drawing Sheets

CENTRAL NERVOUS SYSTEM LABELLING COMPOSITION FOR INTRANASAL ADMINISTRATION AND LABELLING METHOD AND SCREENING METHOD USING CENTRAL NERVOUS SYSTEM LABELLING COMPOSITION FOR INTRANASAL ADMINISTRATION

CROSS-REFERENCE TO RELATED APPLICATIONS

This application is a continuation of International Application No. PCT/JP2010/007465, filed Dec. 24, 2010, which claims the benefit of Japanese Patent Application No. 2009-296329, filed Dec. 25, 2009.

BACKGROUND OF THE INVENTION

1. Field of the Invention

The present invention relates to a central nervous system labelling composition for intranasal administration for the purpose of labelling the central nervous system from the olfactory epithelium by way of the olfactory bulb and by means of intranasal administration, a labelling method using a central nervous system labelling composition for intranasal administration and also a screening method using a central nervous system labelling composition for intranasal administration.

2. Description of the Related Art

A central nervous system labelling composition is transferable to the central nervous system of a living body so as to localize at a particular site of the central nervous system. Thus, it is possible to observe the activity of living central nervous system at a cellular or molecular level and diagnose a disease of a central nervous system by visualizing the state of localization of the central nervous system labelling composition, using an appropriate external observation unit.

Fluorine-18 label fluorodeoxy glucose (FDG) is one of the compounds that are being used for central nervous system labelling. FDG can obtain information useful for diagnosis of brain tumor by visualizing the state of localization thereof in the brain tumor, if any, in the central nervous system by means of positron emission tomography (PET).

The compound disclosed in International Publication No. WO2007/063950 gazette is a near-infrared fluorescent dye having affinity for amyloid β protein. Information useful for diagnosis of the Alzheimer's disease can be obtained by visualizing the site of central nervous system where amyloid β protein is deposited by way of a near-infrared fluorescence observation unit.

U.S. Patent Application Publication No. 2006/0193776 gazette discloses a compound screening method for central nervous systems using zebrafish. According to the patent literature, a dye compound transfers to the brain of an immature zebrafish but not to its central nervous system ten days after fertilization probably because of formation of a blood-brain barrier.

SUMMARY OF THE INVENTION

The transferability of a compound to the brain is limited due to a blood-brain barrier (BBB) or a blood cerebrospinal fluid barrier (BCSFB) and there are many compounds that can transfer into an ordinary tissue but not into the brain. For this reason, there has been a demand for central nervous system labelling compounds that can clearly label the central nervous system without being affected by a BBB or a BCSFB.

Any known central nervous system labelling composition is normally administered by intradermal, intraabdominal, intravenous, intraarterial or cerebrospinal fluid injection. Further, when a developed chemical substance can be distributed also to the entire body other than the central nervous system by way of the circulatory system, it is required to deliberately take safeness relative to anaphylactic shock, heart failure, liver function failure, kidney function failure, skin disorder, respiratory disorder and so on into consideration.

The problem to be solved by the present invention is to provide a central nervous system labelling composition that can be administered by way of a route that neither gives rise to a transfer to the entire body nor significantly affects the living body.

As a result of the intensive research efforts made by the inventors of the present invention to solve the above identified problem, the inventors found a central nervous system labelling composition for intranasal administration that can label the central nervous system from the olfactory epithelium by way of the olfactory bulb and by means of intranasal administration and that transfers only to a small extent to the entire body by way of the circulatory system. The present invention is based on this finding.

Namely, the present invention provides a central nervous system labelling composition for intranasal administration for the purpose of labelling the central nervous system from the olfactory epithelium by way of the olfactory bulb and by means of intranasal administration, characterized by containing at least one compound expressed either by the general formula (1) or the general formula (2) illustrated below as effective component:

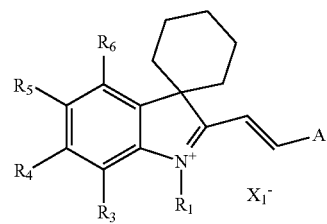

general formula (1)

(in which general formula (1) $R_1$ represents an alkyl group, each of $R_3$ through $R_6$ independently represents a hydrogen atom, an alkyl group, an aryl group, an alkoxy group, a carboxylic acid group, a sulfonic acid group, a heterocyclic group, an amino group or a halogen atom, of which $R_5$ and $R_6$ may be bonded to each other to form a ring, $X_1^-$ represents an anionic group and A represents a general formula (3) or a general formula (4) illustrated below),

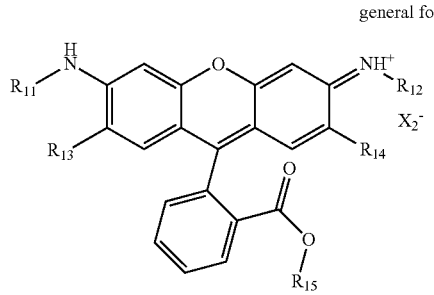

general formula (2)

(in which general formula (2) each of $R_{11}$ through $R_{15}$ independently represents a hydrogen atom or an alkyl group and $X_2^-$ represents an anionic group),

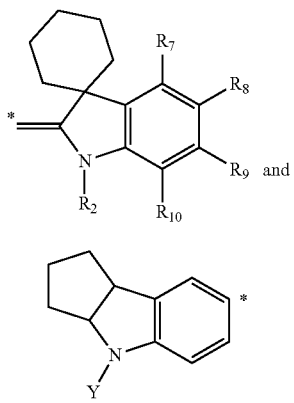

general formula (3)

general formula (4)

(in which general formula (3) $R_2$ represents an alkyl group and each of $R_7$ through $R_{10}$ independently represents a hydrogen atom, an alkyl group, an aryl group, an alkoxy group, a carboxylic acid group, a sulfonic acid group, a heterocyclic group, an amino group or a halogen atom, of which $R_7$ and $R_8$ may be bonded to each other to form a ring) and (in which general formula (4) Y represents an alkyl group).

A central nervous system labelling composition for intranasal administration according to the present invention labels the central nervous system from the olfactory epithelium by way of the olfactory bulb and by means of intranasal administration. Therefore, the present invention enables to highly precisely and easily evaluate and analyze the morphology of the central nervous system and the state of the cells thereof while reducing the influence to the living body that arises as the composition is distributed to the tissues of the entire body by the circulatory system.

Since a central nervous system labelling composition for intranasal administration according to the present invention transfers with time from the olfactory epithelium to the central nervous system by way of the olfactory bulb as a result of intranasal administration, it is possible to visualize how the olfactory nerve cells are linked by monitoring the state of localization of the labelling composition in the transfer process.

Additionally, when the transfer mechanism of a compound to the central nervous system antagonizes the transfer mechanism of a central nervous system labelling composition for intranasal administration according to the present invention, the central nervous system labelling process of a central nervous system labelling composition for intranasal administration according to the present invention is influenced by the coexisting compound. Then, it is possible to find out the possibility of transfer of the compound to the central nervous system after the intranasal administration by detecting the influence. In other words, it is possible to screen out a drug that tends to transfer to the central nervous system as a result of intranasal administration by using a central nervous system labelling composition for intranasal administration according to the present invention.

Further features of the present invention will become apparent from the following description of exemplary embodiments with reference to the attached drawings.

DESCRIPTION OF THE EMBODIMENTS

Figure 1A:
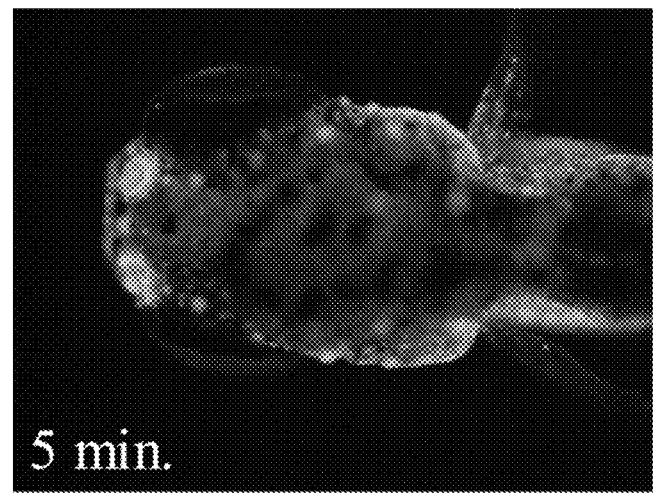
FIG. 1A is a labeled image of the central nervous system observed in Example 1.

Now, the present invention will be described below by way of specific embodiments thereof. However, it should be noted that the embodiments described below are simply exemplar embodiments and by any means do not limit the scope of the present invention.

A central nervous system labelling composition for intranasal administration that is the first embodiment of the present invention is a central nervous system labelling composition for labelling the central nervous system from the olfactory epithelium by way of the olfactory bulb by means of intranasal administration, characterized by containing at least one compound expressed by the general formula (1) or (2) illustrated below.

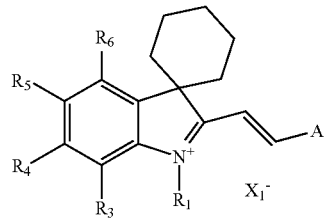

general formula (1)

in which general formula (1) $R_1$ represents an alkyl group, each of $R_3$ through $R_6$ independently represents a hydrogen atom, an alkyl group, an aryl group, an alkoxy group, a carboxylic acid group, a sulfonic acid group, a heterocyclic group, an amino group or a halogen atom, of which $R_5$ and $R_6$ may be bonded to each other to form a ring, $X_1^-$ represents an anionic group and A represents a general formula (3) or a general formula (4) illustrated below, general formula (2)

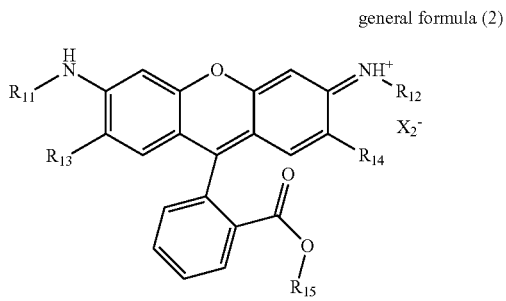

in which general formula (2) each of $R_{11}$ through $R_{15}$ independently represents a hydrogen atom or an alkyl group and $X_2^-$ represents an anionic group, general formula (3)

general formula (4)

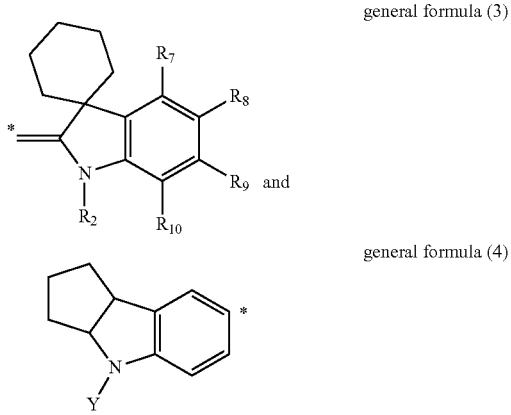

in which general formula (3) $R_2$ represents an alkyl group and each of $R_7$ through $R_{10}$ independently represents a hydrogen atom, an alkyl group, an aryl group, an alkoxy group, a carboxylic acid group, a sulfonic acid group, a heterocyclic group, an amino group or a halogen atom, of which $R_7$ and $R_8$ may be bonded to each other to form a ring and in which general formula (4) Y represents an alkyl group. '*' represents the binding site.

Examples of alkyl group in $R_1$ through $R_2$ in the general formulas (1) and (3) non-limitatively include a methyl group, an ethyl group, a propyl group and a butyl group. The group may further have a substituent provided that the group does not remarkably damage the storage stability of a dye compound according to the present invention.

Examples of alkyl group in $R_3$ through $R_{10}$ non-limitatively include a methyl group, an ethyl group, a propyl group and a butyl group.

Examples of aryl group in $R_3$ through $R_{10}$ non-limitatively include a phenyl group and a naphthyl group.

Examples of alkoxy group in $R_3$ through $R_{10}$ non-limitatively include a methoxy group, an ethoxy group, a propoxy group and a butoxy group.

Examples of heterocyclic group in $R_3$ through $R_{10}$ non-limitatively include a pyridyl group, a pyradyl group and a morpholinyl group.

Examples of amino group in $R_3$ through $R_{10}$ non-limitatively include an unsubstituted amino group, a monosubstituted amino group such as an N-methylamino group or an N-ethylamino group and a disubstituted amino group such as an N,N-dimethylamino group, an N,N-diethylamino group or an N,N-methylpropylamino group.

Examples of halogen atom in $R_3$ through $R_{10}$ non-limitatively include a fluorine atom, a chlorine atom, a bromine atom and an iodine atom.

Examples of ring formed as $R_5$ and $R_6$ and/or $R_7$ and $R_8$ are bonded to each other include a phenyl group.

Examples of anionic group in $X_1^-$ non-limitatively include a halogen ion such as a chloride ion, a bromide ion or an iodide ion, an inorganic acid ion such as a sulfuric acid ion or a phosphoric acid ion and an organic acid ion such as an acetate ion.

Examples of alkyl group in Y in the general formula (4) non-limitatively include a methyl group, an ethyl group, a propyl group and a butyl group.

Examples of alkyl group in $R_{11}$ through $R_{15}$ in the general formula (2) non-limitatively include a methyl group, an ethyl group, a propyl group and a butyl group. The group may further have a substituent provided that the group does not remarkably damage the storage stability of a dye compound according to the present invention.

Examples of anionic group in $X_2^-$ non-limitatively include a halogen ion such as a chloride ion, a bromide ion or an iodide ion, an inorganic acid ion such as a sulfuric acid ion or a phosphoric acid ion and an organic acid ion such as an acetate ion.

Dye compounds expressed by the general formula (1) or (2) that can be used for the purpose of the present invention are commercially available and can be synthesized by a known method.

Preferable exemplar dye compounds expressed by the general formula (1) or (2) are non-limitatively listed below.

general formula (5)

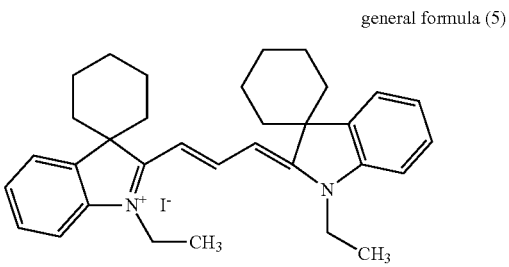

general formula (6)

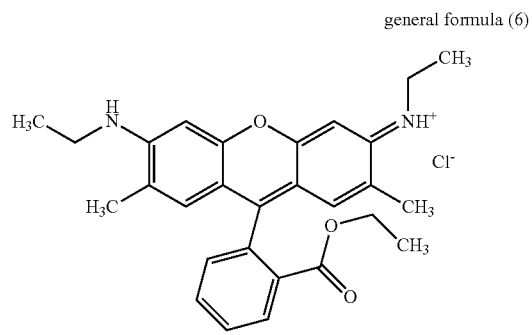

-continued general formula (7)

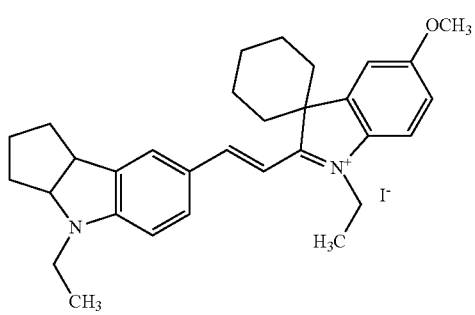

The concentration of the compound contained in the central nervous system labelling composition for intranasal administration according to the present invention is not particularly limited so long as the central nervous system can be detected and may be adjusted according to the target site and the actual compound to be used. Normally, the compound is used with a concentration of not less than 0.001 ng/mL and not more than 100 μg/mL, preferably with a concentration of not less than 0.001 ng/mL and not more than 10 μg/mL, more preferably with a concentration of not less than 0.001 ng/mL and not more than 5 μg/mL.

At least one compound expressed by the general formula (1) or (2) is dissolved into an appropriate solvent so as to be used for a central nervous system labelling composition for intranasal administration according to the present invention. The solvent to be used is preferably an aqueous solvent showing a strong affinity for living bodies, although the solvent is not subjected to any particular limitations so long as the solvent does not adversely affect living bodies. Specific examples of solvent include water, isotonic sodium chloride solution, buffer solutions such as phosphate buffer solution (PBS) and Tris buffer solution, alcoholic solvents such as methanol, ethanol, isopropanol, butanol, ethylene glycol, glycerin and so on, organic solvents such as N,N-dimethylsulfoxide (to be abbreviated as "DMSO" hereinafter) and N,N-dimethylformamide (to be abbreviated as "DMF" hereinafter), cell culture media such as D-MEM (Dulbecco's Modified Eagle Medium and HBSS (Hank's Balanced Salt Solutions) and infusion solutions such as lactated Ringer's solution. The solvent desirably contains 50% water. Two or more than two such solvents may be mixed for use.

The method of preparing a central nervous system labelling composition for intranasal administration according to the present invention is not subjected to any particular limitations. For example, a dense solution of a compound prepared by dissolving the compound in a solvent selected from the above-listed ones may be diluted for use. When the compound is poorly soluble to water, the compound may be dissolved into an appropriate solvent and then, the solution may be diluted by purified water. Particularly preferable solvents include methanol, ethanol and DMSO.

If necessary for controlling the salt concentration and the pH value to make the solution adapted for living bodies, an additive or one or more combined additives may be added to a central nervous system labelling composition for intranasal administration according to the present invention.

The additive to be used for the purpose of the present invention is not subjected to any particular limitations so long as the additive does not adversely affect a central nervous system labelling composition for intranasal administration according to the present invention. Examples of additive that can be used for the purpose of the present invention include moisturizing agents, surface tension adjusting agents, viscosity enhancing agents, salts such as sodium chloride, various pH adjusters, pH buffering agents, antiseptics, antibacterial agents, sweetening agents and perfumes.

pH adjusters to be used for the purpose of the present invention are preferably adapted for adjusting the pH value of the solution to 5 through 9. Examples of pH adjusters non-limitatively include hydrochloric acid, acetic acid, phosphoric acid, citric acid, malic acid, sodium hydroxide, sodium hydrogen carbonate and so on.

(Labelling Targets)

Examples of species in which the central nervous system can be labeled from the olfactory epithelium by way of the olfactory bulb by a central nervous system labelling composition for intranasal administration according to the present invention non-limitatively include vertebrates such as bony fishes (Osteichthyes) including *Takifugu rubripes*, *Takifugu niphobles*, *Tetraodon nigroviridis*, *Oryzias latipes*, zebrafish and so on, amphibians including *Xenopus laevis* and so on, birds including *Gallus gallus domesticus*, quail and so on, small animals such as rat, mouse, hamster and so on, large animals such as goat, pig, dog, cat, cattle, horse and so on, primates such as monkey, chimpanzee, human and so on. In particular, the central nervous system of any of such living bodies can be dyed alive. Human may be omitted from the above species.

Examples of central nervous system that can be labeled by using a central nervous system labelling composition for intranasal administration according to the present invention include central nervous systems composed of cerebrum, mesencephalon, cerebellum, diencephalons, medulla oblongata, spinal cord, optic tract, superior colliculus, pituitary gland, tectospinal tract, reticular formation and so on, such, tissues of such systems in a diseased state, neoplastic tissues due to disease, cancer tissues and so on. If central nervous systems that are different from the above-described ones exist because of difference of species, developmental stage, abnormal development and/or disease, such tissues may also be included.

Cells in the central nervous system non-limitatively include nerve cells, oligodendrocytes, Schwann cells, Purkinje cells, amacrine cells, retinal ganglion cells (RGC), cone cells, astrocytes, granule cells, glial cells, tumor cells thereof and undifferentiated cells (stem cells) thereof.

An administration route that is the second embodiment of the present invention is characterized in that a central nervous system labelling composition for intranasal administration as defined above is administered to the inside of the nasal cavity of a living body. As a central nervous system labelling composition for intranasal administration according to the present invention is administered to the inside of the nasal cavity of a living body, the central nervous system can be labeled with time from the olfactory epithelium by way of the olfactory bulb. In other words, olfactory receptor cells are labeled immediately after the administration, then the olfactory bulb and subsequently the cerebrum (Telencephalon) are sequentially labeled. It is possible to identify a labeled site and dye cells there to see their shapes as a function of the time elapsed after the intranasal administration.

While the method of administering a central nervous system labelling composition for intranasal administration according to the present invention to the inside of the nasal cavity of a living body is not subjected to any particular limitations, for instance, a method of bringing the composition into contact with the nasal mucosa by intranasally spraying or applying it may be employed. When a central nervous system labelling composition for intranasal administration according to the present invention is to be administered to an animal, the mode and the quantity of administration should be appropriately selected according to the weight and the conditions of the animal.

A method of acquiring information by visualizing a label that is the third embodiment of the present invention is characterized in that the method includes a process of dyeing the central nervous system of a living body from the olfactory epithelium by way of the olfactory bulb, using a central nervous system labelling composition for intranasal administration according to the present invention. In other words, the method is characterized by intranasally administering a central nervous system labelling composition for intranasal administration according to the present invention, irradiating light of an excitation wavelength onto an observation site after the elapse of a predetermined time period, observing the generated fluorescence of a longer wavelength and forming an image thereof.

A central nervous system labelling composition for intranasal administration according to the present invention can label any of the cranial nerves including the olfactory nerve. A specific labelling method that can preferably be used for the purpose of the present invention is a method of using a dye or a probe labeled by a radionuclide. Dyeing a cranial nerve is preferable because it can image the distribution and the orientation of the neural tissue of the peripheral nervous system that is connected to that of the central nervous system.

For the purpose of the present invention, to dye cells to see their shapes means that to dye at least one type of cells existing in the central nervous system to enable to determine the cell morphology of each type, for example, by means of fluorescence or the like.

A central nervous system labelling composition for intranasal administration according to the present invention is preferably a fluorescent compound having fluorescent properties. Compounds expressed by any the above-described formulas (5) through (7) also belong to such a category. A method of labelling the olfactory neural circuit or the central nervous system using a central nervous system labelling composition for intranasal administration according to the present invention includes intranasally administering a central nervous system labelling composition for intranasal administration according to the present invention, irradiating light of an excitation wavelength onto an observation site after the elapse of a predetermined time period, observing the generated fluorescence of a longer wavelength than the excitation wavelength and forming an image thereof. Thus, cell morphology information of the labeled site can be obtained.

The observation method to be used for the purpose of the present invention is not subjected to any particular limitations as long as it does not cause any effect to the observed central nervous system, and it can be a method of capturing the state or the change of a sample of a living body as image. For example, it may be a method of irradiating visible light, near-infrared rays or infrared rays to the central nervous system and observing it by means of a camera, a CCD or a laser microscope; a method of irradiating excitation light from an excitation light source onto a sample of a living body typically by means of a fluorescent endoscope and observing emitted fluorescence of the sample of a living body directly or by way of a fluorescent microscope, a fluorescent endoscope, a confocal fluorescent microscope, a multi-photon excitation fluorescent microscope; narrow band imaging (NBI); optial coherence tomography (OCT); or a soft X-ray microscope.

While the wavelength of light to be used for excitation for the purpose of the present invention is not subjected to any particular limitations, the wavelength may vary as a function of the dye compound to be used that is expressed by the general formula (1) or (2). Again, the wavelength is not subjected to any particular limitations so long as the dye compound that is expressed by the general formula (1) or (2) is excited and caused to emit fluorescence efficiently. It is normally 200 through 1,010 nm, preferably 400 through 900 nm, more preferably 480 through 800 nm. When rays in the near-infrared region are employed, normally a wavelength of 600 through 1,000 nm, preferably a wavelength of 680 through 900 nm is employed because light of such a wavelength can advantageously be transmitted through a living body.

The fluorescence excitation light source to be used for the purpose of the present invention is not subjected to any particular limitations and various laser sources may selectively be employed. Light sources that can be used for the purpose of the present invention include dye lasers, semiconductor lasers, ion lasers, fiber lasers, halogen lamps, xenon lamps and tungsten lamps. It is also possible to obtain a preferable excitation wavelength and/or detect only fluorescence by using any of various optical filters.

Thus, it is possible to detect a light emitting site of an individual living body by irradiating the living body and imaging the central nervous system thereof in a state where the central nervous system emits light in the inside. Furthermore, the central nervous system can be observed in a more detailed manner by combining a bright field image obtained by irradiating visible light and a fluorescent image obtained by irradiating excitation light by an image processing unit. The use of a confocal microscope is preferable because optical slice images can be obtained by means of confocal microscope. A multi-photon excitation fluorescent microscope can preferably be employed to observe the inside of a tissue because the microscope can get into a deep spot and shows a high spatial resolution.

A central nervous system labelling composition for intranasal administration according to the present invention can be used as a probe labeled by a radionuclide. The type of radionuclide to be used for labelling is not subjected to any particular limitations and a radionuclide of an appropriate type may be selected according to the mode of operation thereof. More specifically, in the case of observation by PET, examples of radionuclide include positron emission radionuclides such as $^{11}$C, $^{14}$C, $^{13}$N, $^{15}$O, $^{18}$F, $^{19}$F, $^{62}$Cu, $^{68}$Ga and $^{78}$Br, of which $^{11}$C, $^{13}$N, $^{15}$O and $^{18}$F are preferable and $^{11}$C and $^{18}$F are particularly preferable. In the case of observation by SPECT, examples of radionuclide include γ-ray emission radionuclides such as $^{99}$mTc, $^{111}$In, $^{67}$Ga, $^{201}$Tl, $^{123}$I and $^{133}$Xe, of which $^{99}$mTc and $^{123}$I are preferable. When observing an animal other than human, a radionuclide having a long half life such as $^{125}$I can be used. In the case of observation by GREI, $^{131}$I, $^{85}$Sr and $^{65}$Zn can be employed.

The central nervous system labelling composition for intranasal administration that is labeled by a radionuclide can be imaged typically by autoradiography, positron emission tomography (PET) using a positron emission radionuclide, single photon emission computed tomography (SPECT) using any of various γ-ray emission radio nuclides or the like. Alternatively, the composition may be detected by nuclear magnetic resonance imaging (MRI) that utilizes MR signals originating from nuclei of fluorine atoms or $^{13}$C. Furthermore, the composition can be imaged by means of a Compton camera (GREI) capable of simultaneously imaging a plurality of molecules that is regarded as a next generation molecule imaging apparatus. It is also possible to quantify a probe for a central nervous system by means of a liquid scintillation counter, an X-ray film, or an imaging plate.

Additionally, it is possible to observe the blood (or urine or feces) concentration of a central nervous system labelling composition for intranasal administration that is labeled by a radioactive isotope such as $^{14}C$ by means of accelerator mass spectrometry (AMS) in order to obtain pharmacokinetic information on the labeled substance that is unchanged and/or the metabolite thereof, such as the area under the blood concentration-time curve (AUC), the elimination half life (T½), the maximum drug concentration (Cmax), the maximum drug concentration time (Tmax), the volume of distribution, the first pass effect, the bioavailability and the fecal and urinary excretion rate.

The radionuclide may be contained in or bonded to a compound expressed by the general formula (1) or (2). Specific examples of compounds having or bonded to a radionuclide for the purpose of the present invention include compounds expressed by the general formulas (5) (7) that contain a radionuclide or to which a radionuclide is bonded.

For the purpose of the present invention, any popular labelling method using a radionuclide can be employed without limitations. At least part of the elements constituting a compound expressed by the general formula (1) or (2) may be substituted by or bonded to a radionuclide.

When a compound expressed by the general formula (1) or (2) is labeled by a radionuclide, the compound preferably shows a level of radioactivity of about 1 to 100 µCi per 1 mM.

Then, the dose of the central nervous system labelling composition for intranasal administration to be used is not subjected to any particular limitations and may be selected according to the type of the compound and that of the radionuclide used for the labelling.

As the fourth embodiment of the present invention, a central nervous system labelling composition for intranasal administration can be utilized for diagnosis of brain tumor/brain infarction and for diagnosis/therapy/operation using a cerebral endoscope (fiberscope).

A central nervous system labelling composition for intranasal administration according to the present invention can be used as means for uniquely and selectively dyeing the site of a substance to be examined that seems to be an ailing cellular tissue or tumor during a neurosurgical operation and reliably recognizing the difference from normal cells or for observing the change in a tissue due to a disease.

A central nervous system labelling composition for intranasal administration according to the present invention can label a central nervous system without requiring a highly invasive operation of exposing the central nervous system or injecting a dye into the central nervous system or into a tissue connected to the central nervous system. Therefore, the composition can find applications in diagnostic agents that exploit the labelling effect for identifying a labeled site.

Its applications non-limitatively include diagnostic agents for examining the function of the brain and those for diagnosing a brain disease.

The brain diseases that can be diagnosed by such diagnostic agents non-limitatively include Parkinson's disease, Alzheimer's disease, Huntington's chorea, motor neuron disease, tauopathy, cortico basal degeneration (CBD), depressive disorder, epilepsy, migraine, spinocerebellar degeneration (SCD), brain tumor, intracranial hemorrhage and brain infarction.

Specific examples of the fourth embodiment of the present invention will be listed below.

(1) Functional Neuroimaging/Brain Mapping

A central nervous system labelling composition for intranasal administration according to the present invention can be used as probe for functional neuroimaging and brain mapping to replace conventional fMRI, near-infrared functional neuroimaging and endogenous signal imaging. A central nervous system labelling composition for intranasal administration according to the present invention transfers to the inside of the central nervous system, moving through axons of neurons and synaptic clefts. On the other hand, the fluorescent characteristics of a central nervous system labelling composition for intranasal administration according to the present invention change according to mutually dependent molecules of living body and the solvent environment. Therefore, the changes in the activity of cranial nerve cells can be detected by detecting the changes in the fluorescent characteristics.

(2) Olfactory Information Processing/Olfactory Recognition Researches

Animals of many species utilize the olfactory sensation for their eating behaviors, danger avoidance behaviors, reproductive behaviors and other behaviors that are indispensable for survival. While there have been rapid advancements in research on the olfactory sensation since the discovery of the receptor gene family of the olfactory sensation, the neural circuit that governs odor-invoked behaviors such as enticed reactions to "favorite" odors and evasive reactions to "disgusting" odors has not been satisfactorily elucidated.

A central nervous system labelling composition for intranasal administration according to the present invention can be used to visualize the olfactory neural circuit of an animal and elucidate the connections existing in it. It will be possible to draw an odor map of the olfactory bulb and identify the olfactory information transmission paths by making an odorant and a central nervous system labelling composition for intranasal administration according to the present invention coexist and identifying the olfactory neural circuit whose dyeability changes.

(3) Photosensitizer (Photodynamic Therapy: PDT)

A central nervous system labelling composition for intranasal administration according to the present invention can be used as photosensitizer. A photosensitizer is activated when irradiated with photoactivating light and the photosensitizer itself or some other chemical species (e.g., oxygen) are transformed into cytotoxic species, which by turn kills the target cells of the site irradiated with light or reduces the reproductive potential thereof.

Therefore, a central nervous system labelling composition for intranasal administration according to the present invention can be used for diagnostic as well as therapeutic applications on the basis of a label in the central nervous system.

A screening method, which is the fifth embodiment of the present invention, is characterized by detecting a compound acting in vivo on the central nervous system by means of a central nervous system labelling composition for intranasal administration according to the present invention.

A central nervous system labelling composition for intranasal administration according to the present invention can be used to evaluate in vivo the transferability to the central nervous system via nose of a compound to be screened out and the safety thereof by using a zebrafish that is a small bony fish.

Zebrafish has been acknowledged in recent years as the third animal model, following mouse and rat, in the United States of America and in the United Kingdom and it has been clarified that zebrafish's genome arrangement is 80% identical with that of human and the number of zebrafish's genes is substantially same as the number of human genes and that zebrafish's principal organs and tissues resemble to human counterparts in terms of development and structure. Because the process of differentiation of zebrafish's parts (organs such as heart, liver, kidney and digestive system) from a fertilized embryo can be observed through its transparent body, it is particularly preferable to use a zebrafish as animal model for screening.

For the purpose of the present invention, "detecting a compound acting on the central nervous system" means detecting if there is a compound acting on the central nervous system or not and, if there is, its characteristics by observing the change, if any, in the labelability of a central nervous system labelling composition for intranasal administration according to the present invention when the compound to be looked into (the compound to be screened out) is made to act on the central nervous system by using the central nervous system labelling composition for intranasal administration. As a specific example, a screening method of bringing a compound to be screened out and a zebrafish into contact with each other and observing the influence on the ability of dyeing the brain of a zebrafish of an intranasally administered central nervous system labelling composition for intranasal administration according to the present invention may be effective for such a purpose.

While the method for bringing a compound to be screened out into contact with a zebrafish to be used for the purpose of the present invention is not subjected to any particular limitations, it may be a method of putting a compound to be screened out into the feeding water of zebrafish for administration when the compound to be screened out is water soluble, whereas it may be a method of dispersing a compound to be screened out alone in the feeding water for administration, a method of administering it with a small amount of surfactant or DMSO, a method of mixing it with a bait of zebrafish and orally administering it or a non-oral administration method such as injection when the compound to be screened out is water insoluble. Preferably, a method of putting a compound to be screened out into the feeding water of zebrafish for administration is employed from the viewpoint of easiness.

A compound to be screened out generically refers to a compound that biochemically acts on a living body. Such compounds non-limitatively include drugs, organic compounds, therapeutic agents, investigational products, agricultural chemicals, cosmetics, environment polluting substances, endocrine disruptors and candidate compounds for such. Drugs, therapeutic agents and candidate compounds for such as described above refer to drugs for curing Parkinson's disease, Alzheimer's disease, Huntington's chorea, motor neuron diseases, tauopathy, cortico basal degeneration (CBD), depressive disorder, epilepsy, migraine, spinocerebellar degeneration (SCD), brain tumor, intracranial hemorrhage, brain infarction and so on and candidate compounds for such as well as compounds that accelerate or suppress the transfer of any of such compounds to the central nervous system via nose.

Additionally, such compounds include drugs for curing disorders of the olfactory sensation attributable to any of the above listed diseases and candidate compounds for such.

Zebrafishes that can be used for the purpose of the present invention are not limited to wild type zebrafishes but any of various disease model zebrafishes can be used depending on the object of screening. For instance, disease model zebrafishes can be used to find out the effects of new drug candidate compounds by observation and apply it to screening out a therapeutic drug or a prophylactic drug.

Additionally, it is possible to evaluate the speed at which a compound to be screened out transfers to the central nervous system of a zebrafish via nose by observing the rate at which a dye dyes the brain of the zebrafish via nose when a central nervous system labelling composition for intranasal administration according to the present invention is intranasally administered and coexist with the compound to be screened out.

A small bony fish can be used for a screening method according to the present invention. Small bony fishes that can be used for the screening method of the present invention are not subjected to any particular limitations. For example, such bony fishes include zebrafish, puffer fish, gold fish, killifish, giant rerio and so on. The use of small bony fishes is preferable because they are very advantageous relative to mouse and rat in terms of growing speed and cost. Particularly, the genome of zebrafish has been substantially completely deciphered and it is easy to feed and reproduce zebrafishes, which then can be distributed at low cost. Moreover, the basic structure of the principal organs and tissues of a zebrafish is formed in 48 through 78 hours after fertilization. Therefore, the use of zebrafishes is particularly preferable.

(Extrapolatability to Humans)

A central nervous system labelling composition for intranasal administration according to the present invention is applicable to humans. The extrapolatability thereof to humans can be confirmed by seeing the whole approximation given on the basis of recognition of the similarities and the differences of central nervous system between humans and experiment animals. While several examples are given below, the present invention is by no means limited thereto.

(1) To confirm the similarities by dyeing the central nervous system of human and that of a living biological sample other than human. Living samples other than human that can be used for the purpose of the present invention include mammals such as mouse, hamster, rat, guinea pig, rabbit, dog, pig, cat and monkey and bony fishes such as zebrafish.

(2) To confirm the dyeability of the central nervous system by using an immobilized tissue slice of a human and that of a living biological sample other than human and thereby confirm that the human central nervous system shows a dyeability similar to that of the central nervous system of the living biological sample.

(3) To confirm the dyeability of the central nervous system by using an immobilized tissue slice of a human.

It is possible to confirm that a central nervous system labelling composition for intranasal administration according to the present invention is applicable to humans by conducting the above-described three confirming operations.

Alternatively, the extrapolability to humans can be confirmed by radioisotope-labelling a central nervous system labelling composition for intranasal administration according to the present invention, internally administering a minimal amount thereof to a human and ensuring localization thereof to the central nervous system. This technique is referred to as microdosing.

A still alternatively technique includes (1) identifying the target living molecules or the dyeing mechanism of a central nervous system labelling composition for intranasal administration according to the present invention by means of the central nervous system of a living biological sample other than human; (2) identifying the human living molecules homologous with the target living molecules or the dyeing molecule mechanism; (3) introducing the human living molecules or the dyeing mechanism into an experiment animal by gene modification and (4) confirming that the central nervous system of the obtained experiment animal is dyed by way of the introduced living molecule or dyeing mechanism.

A zebrafish can particularly preferably be used as biological sample other than human. Many vertebrates preserve common features of central nervous system very well from the anatomical, histological and biochemical point of view very well as well as from the development point of view. Therefore, the use of zebrafishes provides a remarkable advantage because the feeding cost is low and the amount of the compound to be used can be very small if compared with the use of mice. Additionally, it has been proved that the central nervous system of zebrafish shows a high degree of homology with that of human not only in terms of shape but also in terms of molecular level. From the above, it is preferable to confirm the extrapolability to humans of a central nervous system labelling composition for intranasal administration according to the present invention by using zebrafishes.

EXAMPLES

The present invention will be described in greater detail by way of examples. However, it should be noted that the examples are only to promote understanding of the present invention and by no means limit the scope of the present invention. Unless noted otherwise, "%" refers to a mass percent.

Example 1

Distilled water was added to a 1 mg/mL DMSO solution of compound 1 (as expressed by the formula (5) above) to obtain a dye solution 1 containing the compound 1 to a concentration of 200 ng/mL. 1 mL of the dye solution 1 and a 7-day-old (7 dpf) juvenile fish of zebrafish were put into an arbitrarily selected well of a 24-hole multi plate (available from IWAKI) and left there for an hour. Thereafter, the dye solution 1 in the well was removed and an operation of replacing it with 1 mL of distilled water was repeated three times in ten minutes. The elapsed time after the last solution replacing operation was measured and the juvenile fish was taken out from the well when a predetermined time period had elapsed. The juvenile fish was buried in 5% low melting-point agarose gel on a glass slide to restrict any movement and the dyed state of the central nervous system of the zebrafish was observed from a lateral side and the vertex by using fluorescent microscope (MZ16FA: available from Leica). The central nervous system was observed by means of a confocal microscope (Pascal Exciter: available from Zeiss). After the observation, the zebrafish was returned into the well and repeatedly observed thereafter at regular time intervals.

Figure 1B:
FIG. 1B is a labeled image of the central nervous system observed in Example 1.
Figure 1C:
FIG. 1C is a labeled image of the central nervous system observed in Example 1.

As a result, a dyeability was confirmed that firstly the nasal cavity, then the olfactory bulb and finally the central nervous system were sequentially dyed as illustrated in FIGS. 1A, 1B and 1C.

Figure 2:
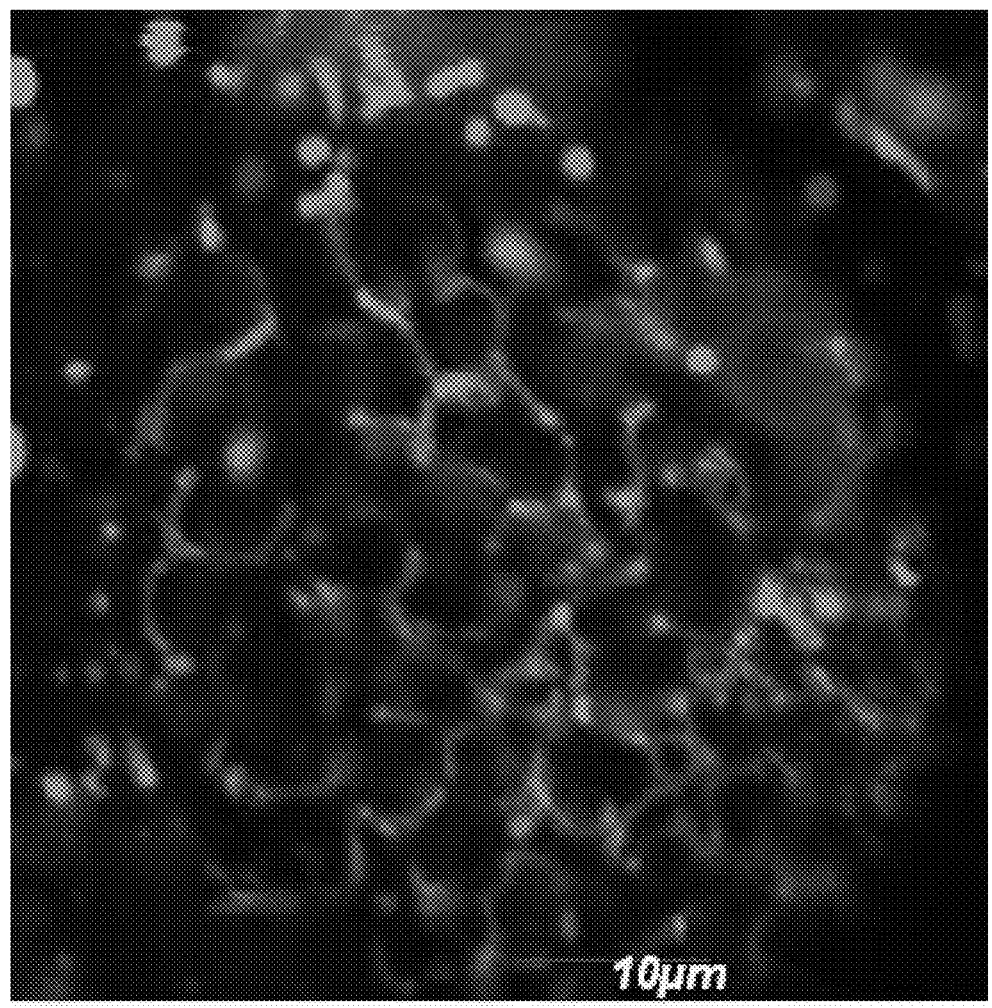
FIG. 2 is a labeled image of the central nervous cell observed in Example 1.

Additionally, it was confirmed that nerve cells of the central nervous system were also dyed as illustrated in FIG. 2.

Example 2

Dye solution 2 whose concentration of the compound 2 is 500 ng/mL was obtained by adding distilled water to 1 mg/mL DMSO solution of compound 2 (as expressed by the formula (6) above). Operations same as those of Example 1 were conducted except that the dye solution 2 was used in place of the dye solution 1 to observe the central nervous system.

Figure 3A:
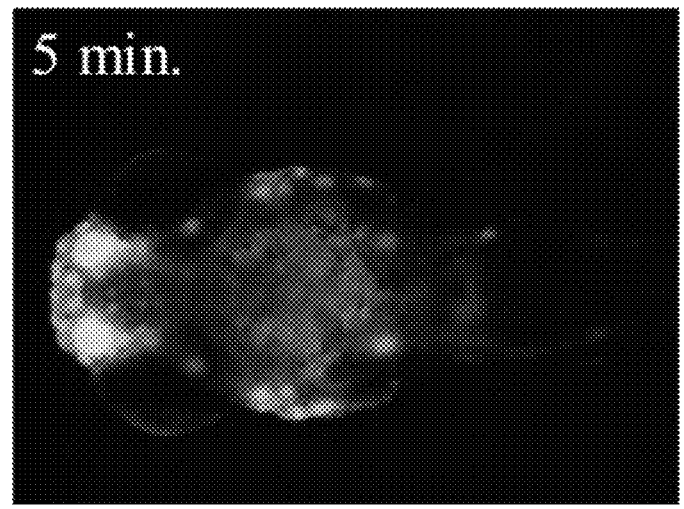
FIG. 3A is a labeled image of the central nervous system observed in Example 2.
Figure 3B:
FIG. 3B is a labeled image of the central nervous system observed in Example 2.
Figure 3C:
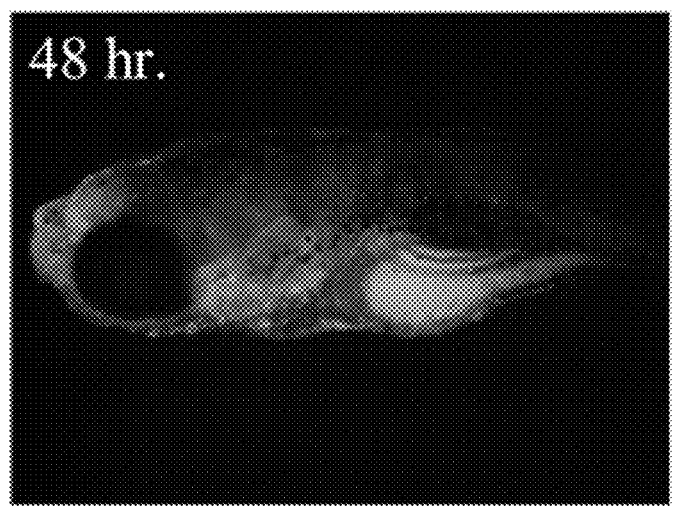
FIG. 3C is a labeled image of the central nervous system observed in Example 2.
Figure 4A:
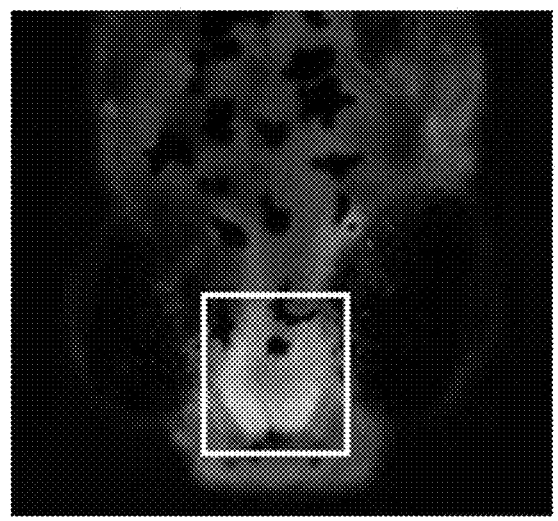
FIG. 4A is a labeled image of the central nervous cell observed in Example 2.
Figure 4B:
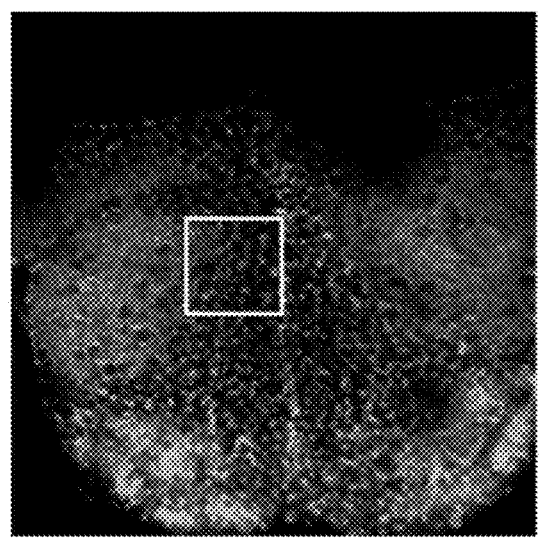
FIG. 4B is a labeled image of the central nervous cell observed in Example 2.
Figure 4C:
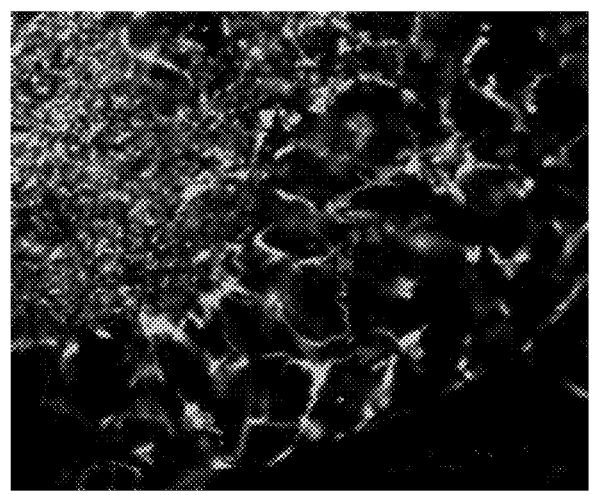
FIG. 4C is a labeled image of the central nervous cell observed in Example 2.

As a result, a dyeability was confirmed that firstly the nasal cavity, then the olfactory bulb and finally the central nervous system were sequentially dyed as illustrated in FIGS. 3A, 3B and 3C. Additionally, a dyeability was confirmed that nerve cells of the central nervous system were also dyed as illustrated in FIGS. 4A, and 4B, which is an enlarged view of the inside of the frame in FIGS. 4A, and 4C, which is an enlarged view of the inside of the frame in FIG. 4B.

Comparative Example 1

Dye solution 3 whose concentration is 500 ng/mL was obtained by adding distilled water to 1 mg/mL DMSO solution of fluorescein. Operations same as those of Example 1 were conducted except that the dye solution 3 was used in place of the dye solution 1 to observe the central nervous system.

Figure 5:
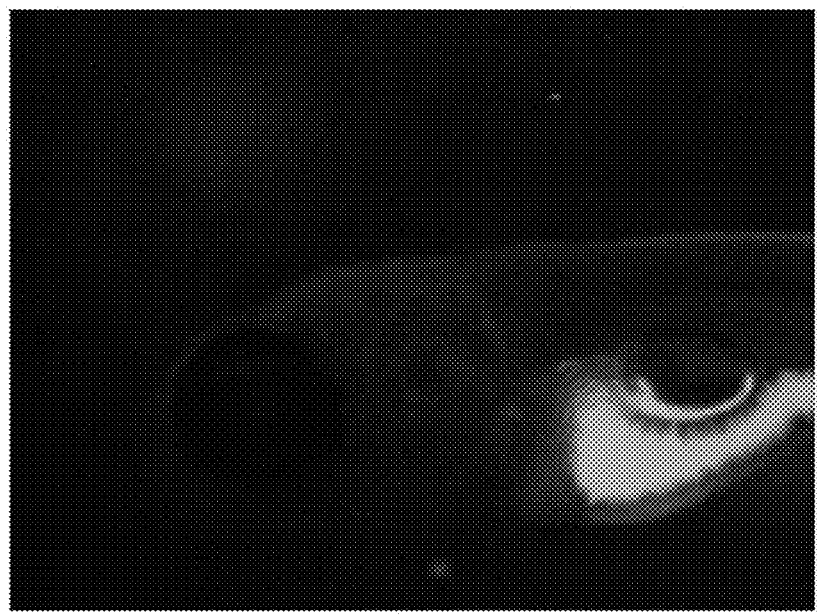
FIG. 5 is an observation image of the zebrafish observed in Comparative Example 1.

As a result, no transfer with time of dyeability to the central nervous system was observed as illustrated in FIG. 5.

Example 3

Compound 3 (as expressed by the formula (7) above) was synthesized by a method described in Japanese Patent Application Laid-Open No. 2010-169677. Dye solution 4 whose concentration of the compound 3 is 500 ng/mL was obtained by adding distilled water to 1 mg/mL DMSO solution of compound 3. Operations same as those of Example 1 were conducted except that the dye solution 4 was used in place of the dye solution 1 to observe the central nervous system.

Figure 6A:
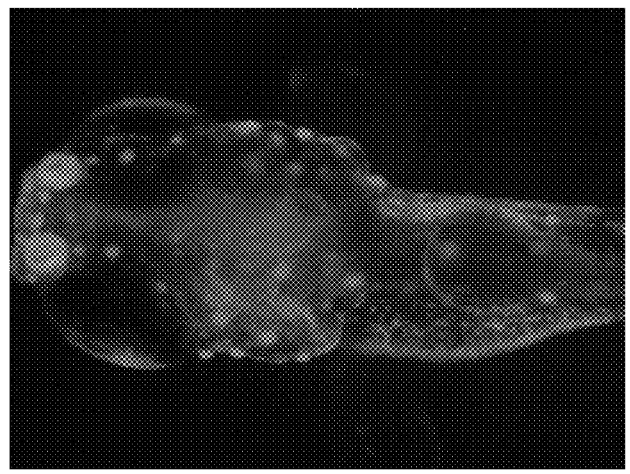
FIG. 6A is a labeled image of the central nervous system observed in Example 3.
Figure 6B:
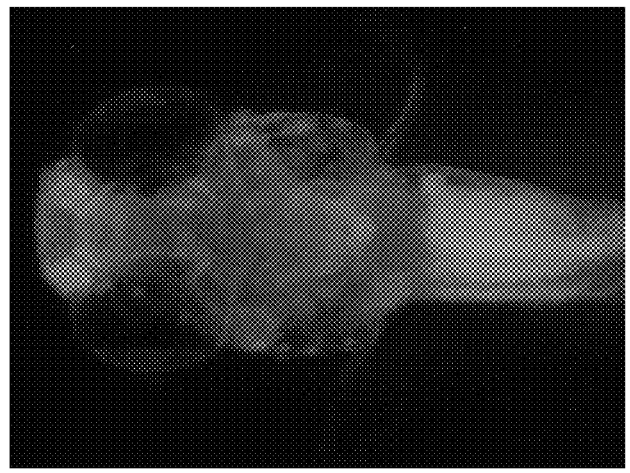
FIG. 6B is a labeled image of the central nervous system observed in Example 3.
Figure 6C:
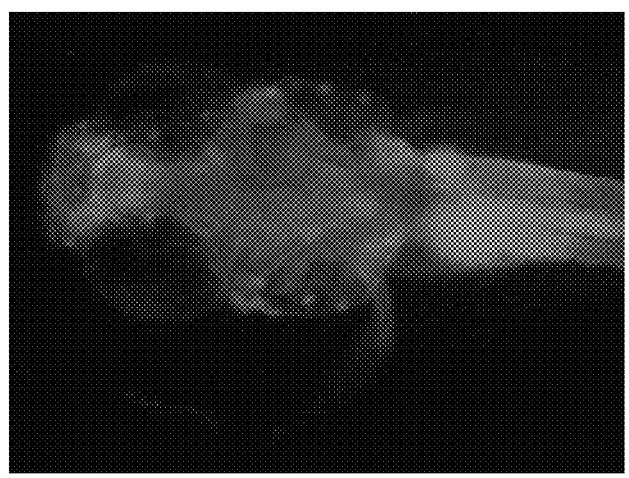
FIG. 6C is a labeled image of the central nervous system observed in Example 3.
Figure 7:
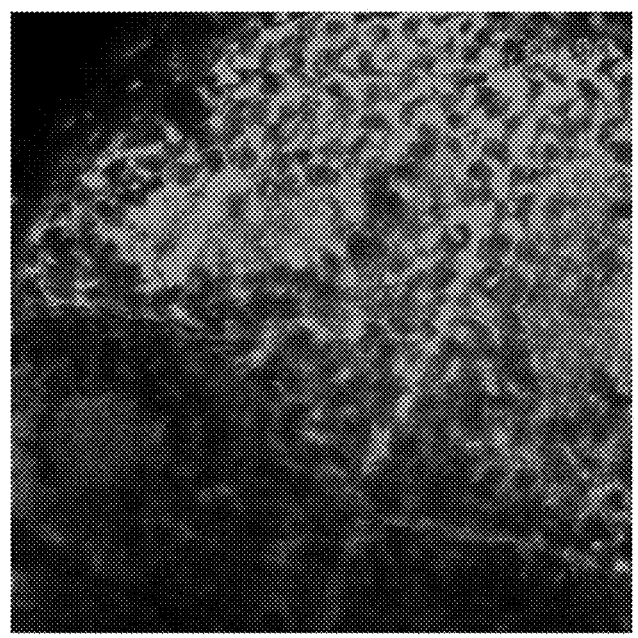
FIG. 7 is a labeled image of the central nervous cell observed in Example 3.

As a result, a dyeability was confirmed that firstly the nasal cavity, then the olfactory bulb and finally the central nervous system were sequentially dyed as illustrated in FIGS. 6A, 6B and 6C. Additionally, the dyeability was confirmed that nerve cells of the central nervous system were also dyed as illustrated in FIG. 7.

The present invention provides a central nervous system labelling composition for intranasal administration that labels the central nervous system of a living biological sample by way of a new administration route and can highly sensitively image the shapes of the cells of the central nervous system. The labelling composition will become an indispensable material for researches of central nervous system regions and techniques of imaging central nervous systems. It also enables to evaluate drug discoveries relating to the diseases of central nervous system over time. Additionally, since a central nervous system labelling composition for intranasal administration according to the present invention enables to conduct high precision screenings at a high throughput, an effective technical basis for dramatically promoting researches on the central nervous system and making them industrially viable will be provided.

The present application claims the benefit of Japanese Patent Application No. 2009-296329, filed on Dec. 25, 2009, the disclosures of which are partly incorporated herein by reference.

What is claimed is:

1. A method of labeling a central nervous system of a living body by dyeing from an olfactory epithelium by way of an olfactory bulb, the method comprising intranasally administering a central nervous system labeling composition comprising a compound of formula (1):

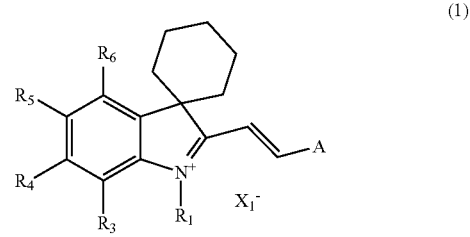

(1)

where $R_1$ represents an alkyl group; each of $R_3$ through $R_6$ independently represents a hydrogen atom, an alkyl group, an aryl group, an alkoxy group, a carboxylic acid group, a sulfonic acid group, a heterocyclic group, an amino group, or a halogen atom, of which $R_5$ and $R_6$ may be bonded to each other to form a ring; $X_1^-$ represents an anionic group; and A represents a formula (4):

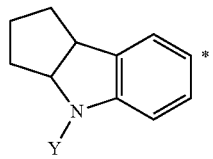

(4)

where Y represents an alkyl group; and * represents a binding site.

2. A screening method for detecting in vivo a compound acting on a central nervous system, the method comprising:
intranasally administering a central nervous system labeling composition comprising a compound of formula (1):

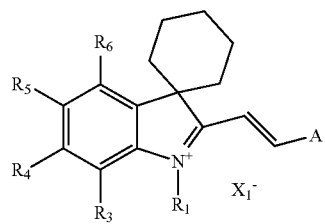

(1)

where $R_1$ represents an alkyl group; each of $R_3$ through $R_6$ independently represents a hydrogen atom, an alkyl group, an aryl group, an alkoxy group, a carboxylic acid group, a sulfonic acid group, a heterocyclic group, an amino group, or a halogen atom, of which $R_5$ and $R_6$ may be bonded to each other to form a ring; $X_1^-$ represents an anionic group; and A represents a formula (4):

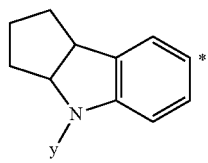

(4)

where Y represents an alkyl group; and * represents a binding site; and detecting in vivo the compound acting on the central nervous system using the administered central nervous system labeling composition.

3. The method according to claim 1, wherein the compound of formula (1) is a fluorescent compound.

4. The method according to claim 1, wherein the compound of formula (1) is labeled by a radionuclide.

5. The method according to claim 2, wherein the compound of formula (1) is a fluorescent compound.

6. The method according to claim 2, wherein the compound of formula (1) is labeled by a radionuclide.

* * * * *